(12) United States Patent
Kates

(10) Patent No.: US 7,058,182 B2
(45) Date of Patent: Jun. 6, 2006

(54) APPARATUS AND METHODS FOR HEARING AID PERFORMANCE MEASUREMENT, FITTING, AND INITIALIZATION

(75) Inventor: James Mitchell Kates, Niwot, CO (US)

(73) Assignee: GN ReSound A/S, Taastrup (DK)

( * ) Notice: Subject to any disclaimer, the term of this patent is extended or adjusted under 35 U.S.C. 154(b) by 209 days.

(21) Appl. No.: 10/150,242

(22) Filed: May 17, 2002

(65) Prior Publication Data

US 2002/0176584 A1    Nov. 28, 2002

Related U.S. Application Data

(63) Continuation-in-part of application No. 09/413,732, filed on Oct. 6, 1999, now Pat. No. 6,792,114.

(51) Int. Cl.
*H04R 29/00* (2006.01)

(52) U.S. Cl. .................. 381/60; 381/312; 600/559; 73/585

(58) Field of Classification Search .................. 381/60, 381/312; 600/559; 73/585
See application file for complete search history.

(56) References Cited

U.S. PATENT DOCUMENTS 6,118,877 A * 9/2000 Lindemann et al. .......... 381/60
6,134,329 A * 10/2000 Gao et al. ..................... 381/60

* cited by examiner

*Primary Examiner*—Huyen Le
*Assistant Examiner*—Con P. Tran
(74) *Attorney, Agent, or Firm*—Macheledt Bales & Heidmiller, LLP; Jennifer L. Bales

(57) ABSTRACT

A digital hearing aid according to the present invention is capable of measuring its own performance. The measurement and initialization capability may be entirely integral to the hearing aid, or an external processor may be used to download the measurement program and the run time program, and assist in computing the parameters. The hearing aid includes a test signal generator for feeding a test signal into the hearing aid amplifier. The response to the test signal is acquired at a specific point in the hearing aid, depending upon what aspect of performance is to be measured. Various elements of the hearing aid and/or the hearing aid feedback may be bypassed. The hearing aid further includes the capability of initializing hearing aid parameters based upon the performance measurements.

11 Claims, 16 Drawing Sheets

APPARATUS AND METHODS FOR HEARING AID PERFORMANCE MEASUREMENT, FITTING, AND INITIALIZATION

This application is a continuation in part of patent application Ser. No. 09/413,732 filed on Oct. 6, 1999 now U.S. Pat. No. 6,792,114 for Integrated Hearing Aid Performance Measurement and Initialization System. U.S. Pat. No. 6,219,427, issued Apr. 17, 2001 and entitled "Feedback Cancellation Improvements" is incorporated herein by reference.

BACKGROUND OF THE INVENTION

1. Field of the Invention

The present invention relates to apparatus and methods for hearing aid performance measurement, fitting, and initialization.

2. Description of the Prior Art

In general, hearing aid performance measurements, whether on the production line or in the individual wearer's ear, have used an external test system that generates the test signal and analyzes the response. For example, an audiogram is a major tool used in fitting a hearing aid. An audiogram is a measurement of hearing loss, typically plotted as loss in dB as a function of frequency. Measuring an audiogram typically involves playing a set of tones through headphones while adjusting the level and frequency of the tones, and having the patient indicate whether each tone can be heard or is inaudible. Computer systems for measuring audiograms are commercially available. U.S. Pat. No. 4,548,082 to Englebretson et al describes one method for measuring an audiogram.

The measurement of the frequency response of a hearing aid in the ear, for example, typically requires the use of external signal generating and measurement equipment (Egolf, D. P., Tree, D. R., and Feth, L. L., 1978, "Mathematical predictions of electroacoustic frequency response of in situ hearing aids", J. Acoust. Soc. Am., Vol. 63, pp 264–271; Bade, P. F., Engebretson, A. M., Heidbreder, A. F., and Niemoeller, A. F., 1984, "Use of personal computer to model the electroacoustics of hearing aids", J. Acoust. Soc. Am., Vol. 75, pp 617–620; Sanborn, P-E, 1998, "Predicting hearing aid response in real ears", J. Acoust. Soc. Am., Vol. 103, pp 3407–3417). Measurements of the feedback path from the receiver back to the hearing aid microphone also have required the use of external equipment (Egolf, D. P., Howell, H. C., Weaver, K. A., and Barker, S., 1985, "The hearing aid feedback path: Mathematical simulations and experimental verification", J. Acoust. Soc. Am., Vol. 78, pp 1578–1587), as does the determination of the maximum output signal level (Revit, L. J., 1994, "Using coupler tests in the fitting of hearing aids", in *Strategies for Selecting and Verifying Hearing Aid Fittings*, ed. by M. Valente, New York: Thieme Medical Publishers).

A conventional digital hearing aid is shown in FIG. 1A (prior art). Input sound signal 152 is converted into an audio signal by microphone 154. Hearing aid processor 156 is a digital signal processor (analog to digital conversion at the input and digital to analog conversion at the output are omitted for clarity). The processed audio signal is amplified by amplifier 158 and converted back into a sound signal 162 by receiver 160. Conventional digital hearing aids like hearing aid 110 use digital signal processing for the run time system, but still rely on conventional measurement equipment for measuring the hearing aid response and setting the processing parameters. Most digital hearing aids do not contain a programmable DSP circuit, but instead use a dedicated processor that can only perform the run time processing operations (Schweitzer, C., "Development of digital hearing aids", Trends in Amplification, Vol 2, pp 41–77). These hearing aids are therefore incapable of performing any measurements, calibration, or parameter initialization.

An example of a conventional hearing aid test system 101 is illustrated in FIG. 1B (prior art). The hearing aid 110 to be evaluated is placed in a test box 102. The input to hearing aid 110 is an acoustic test signal 109 from loudspeaker 108, also contained in test box 102. Hearing aid 110 is configured to perform the desired signal processing function, such as linear gain or multiband compression. The hearing aid output is an acoustic signal that is then piped to acoustic coupler 114 via a piece of tubing 113. The acoustic coupler consists of a microphone 118 placed at the end of a cavity 116. An external computer 104 controls the generation of test signal 109 and acquires and processes the microphone response 120. Display 116 displays test results. A commercial hearing aid test system that conforms to this basic design is the Fonix 6500, manufactured by Frye Electronics, Inc, Tigard, Oreg. 97223.

For independently performing measurements, the digital hearing aid must be able to accept a program for generating a test signal and recording the response as well as accept the program for the run time processing. A need remains in the art for apparatus and methods for integrated hearing aid performance measurement, fitting, and initialization.

SUMMARY OF THE INVENTION

It is an object of the present invention to provide apparatus and methods for integrated hearing aid performance measurement, fitting, and initialization.

In addition to providing digital processing of the audio signal being amplified to compensate for the hearing loss, the programmable DSP circuit of a hearing aid according to the present invention is also used to measure the characteristics of the hearing aid on the production line or fitted to the individual ear. Such a hearing aid might perform measurements such as maximum output signal level, distortion, or the response characteristics of the microphone or receiver. By using the signal processing system described herein, these and other tests can be performed all or in part by the hearing aid under test. A test program is loaded into the hearing aid and the tests are performed. Then the program used for the run time amplification, along with any processing parameters set during the tests, is loaded into the hearing aid memory.

Improvements according to the present invention include improvements to the fitting and initialization of the hearing aid. With regard to fitting and initializing the feedback cancellation hearing aid, the feedback path model determined during initialization may be used to set the maximum gain allowable in the hearing aid. This maximum stable gain can be used to assess the validity of the hearing aid design, by determining whether the the recommended gain for that design exceeds the maximum stable gain. Further, the hearing aid fitting in the ear canal may be tested for leakage, by testing whether the maximum stable gain computed for the hearing aid with its vent hole blocked is substantially higher than the maximum stable gain computed for the hearing aid with its vent open.

Another fitting and initialization feature allows the use of the error signal plotted versus time in the feedback cancellation system as a convergence check of the system, or the amount of feedback cancellation can be estimated by comparing the error at the end of convergence to that at the start of convergence. The error signal may also be used to do an iterative selection of optimum bulk delay in the feedback path, with the optimum delay being that which gives the minimum convergence error. Or, the bulk delay may be set by choosing a preliminary delay, allowing the zero model coefficients to adapt, and adjusting the preliminary delay so that the coefficient having the largest magnitude is positioned at a desired tap location.

DETAILED DESCRIPTION OF THE PREFERRED EMBODIMENT

Figure 1A:
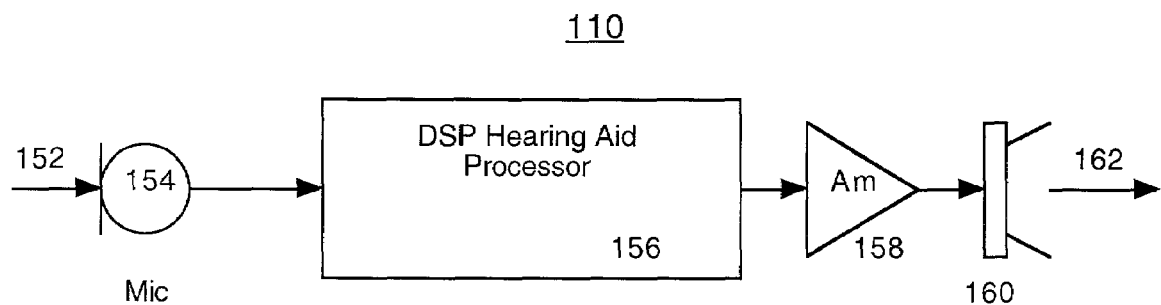
FIG. 1A (prior art) shows a conventional hearing aid.
Figure 1B:
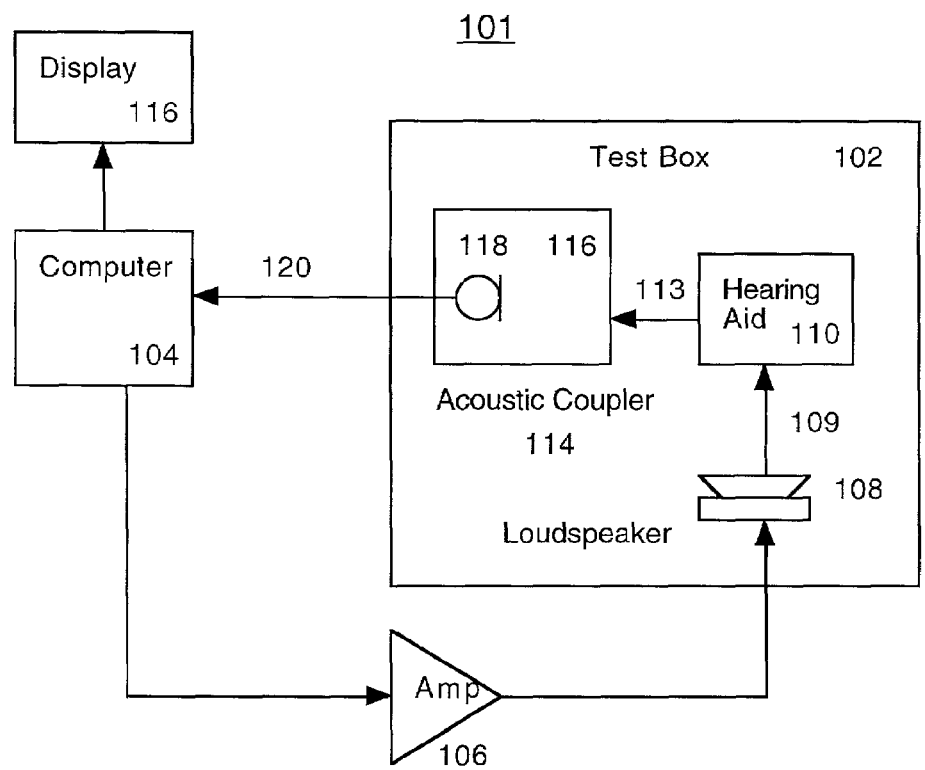
FIG. 1B (prior art) shows a conventional hearing aid test system.
Figure 2A:
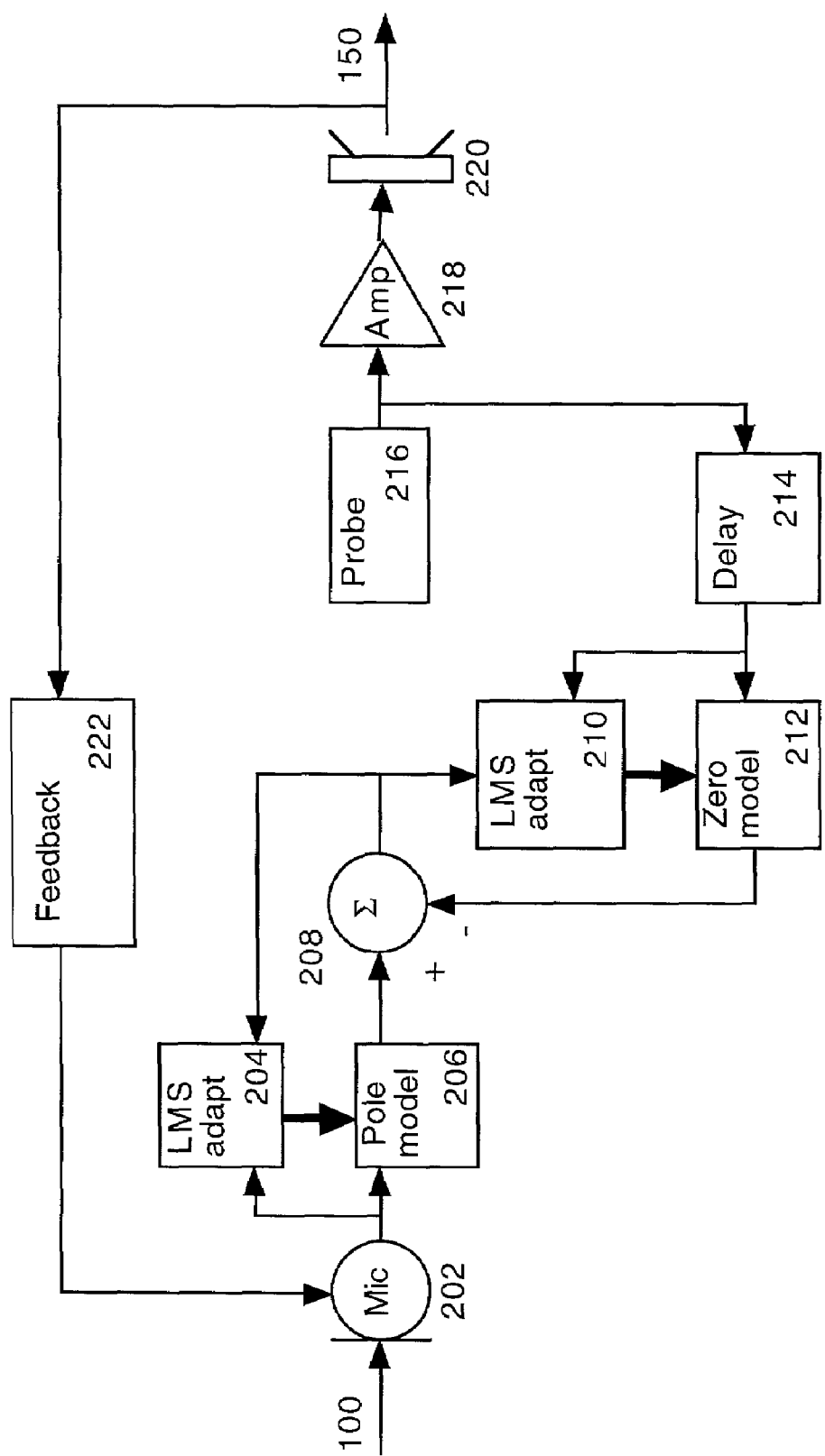
FIG. 2A (prior art) is a block diagram showing a hearing aid with feedback cancellation, configured for initial determination of zero filter coefficients at start-up.
Figure 2B:
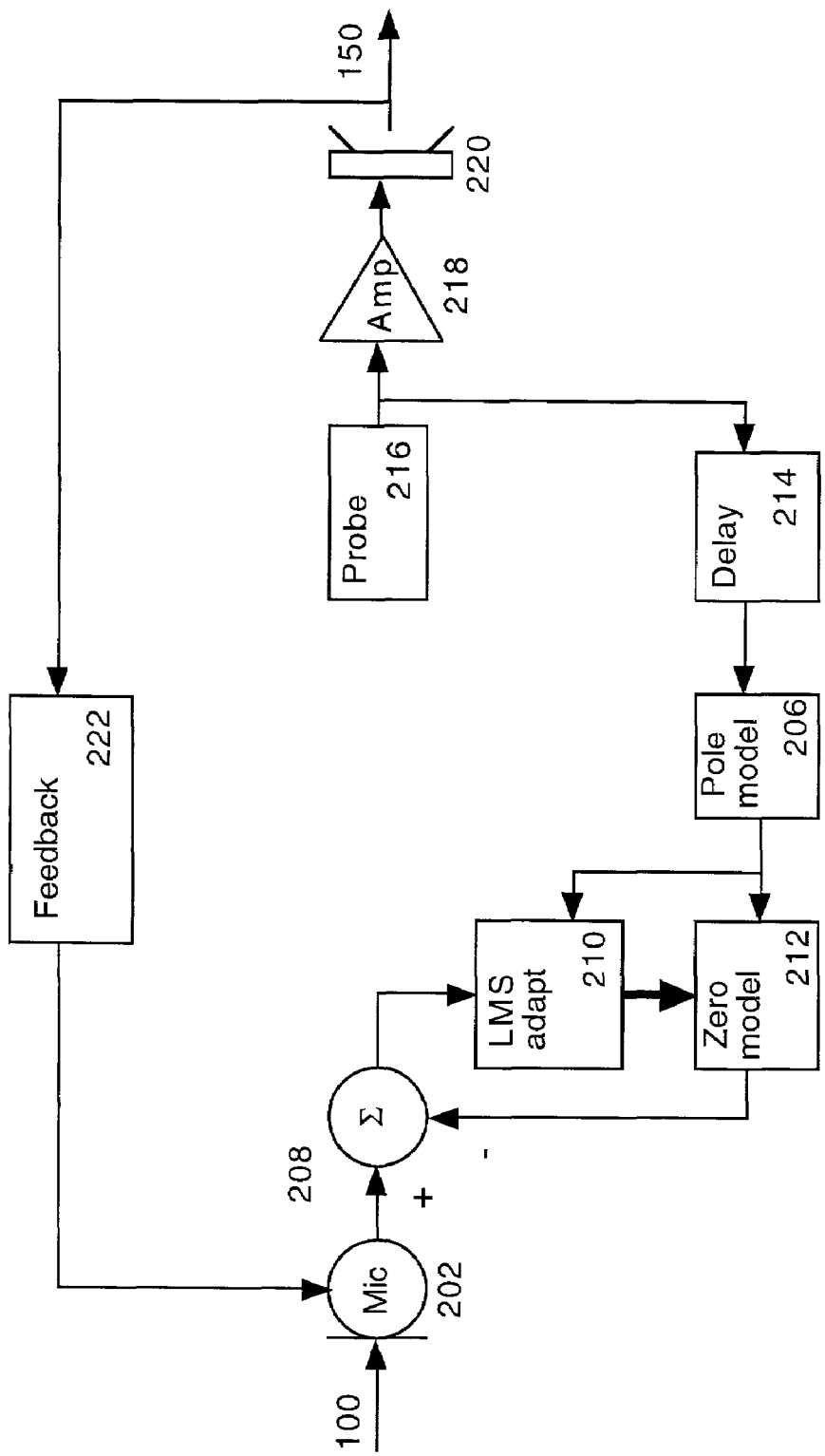
FIG. 2B (prior art) is a block diagram showing the hearing aid of FIG. 2A, configured for optimizing zero filter coefficients at start-up.
Figure 3:
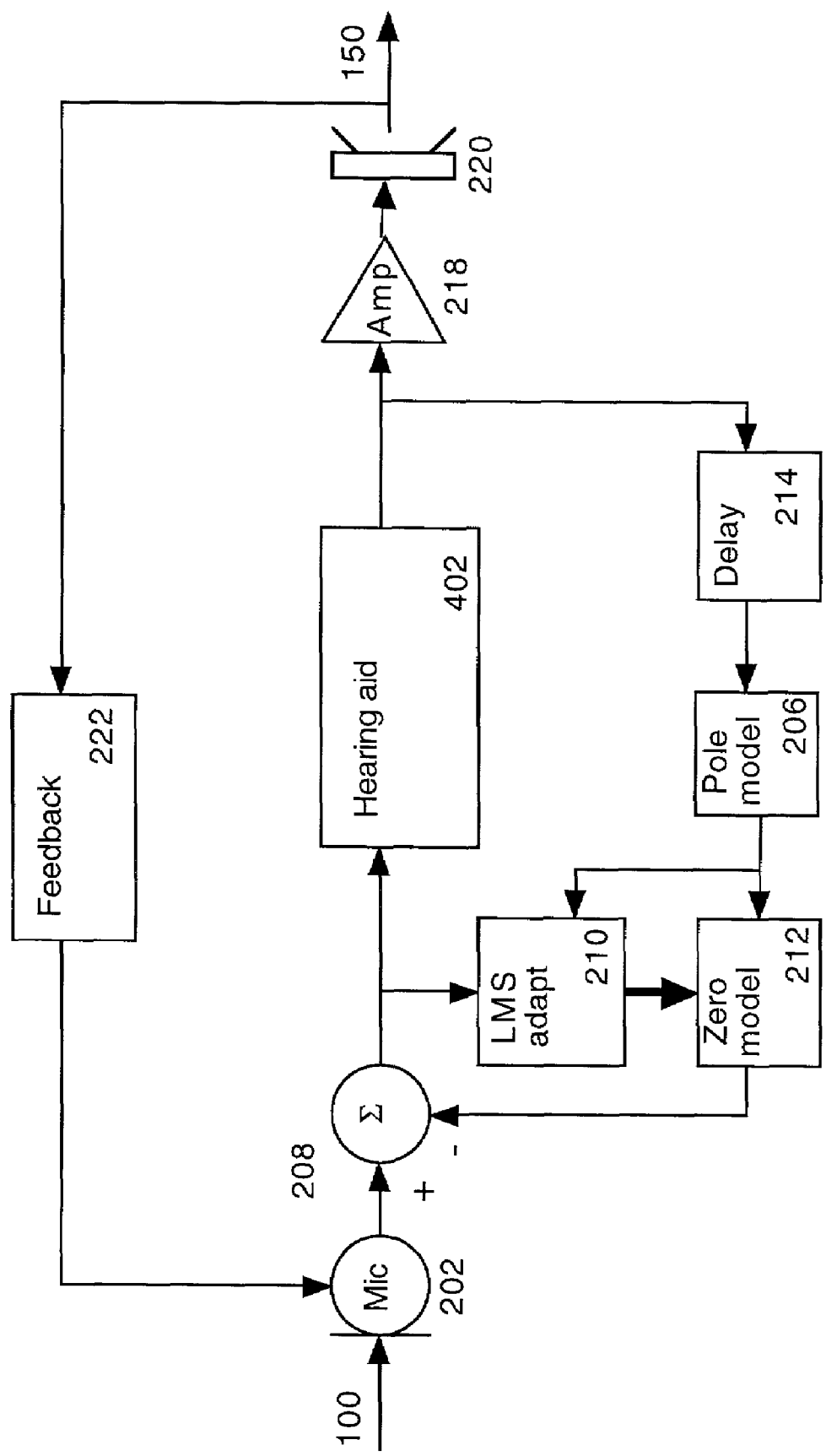
FIG. 3 (prior art) is a block diagram showing the hearing aid of FIG. 2A, configured for operation.

FIGS. 2A, 2B, and 3 (prior art) are block diagrams showing a feedback cancellation hearing aid during initialization and operation. U.S. Pat. No. 6,219,4278, issued Apr. 17, 2001, entitled "Feedback Cancellation Improvements" and incorporated herein by reference, describes this embodiment in greater detail. A brief description follows.

The IIR filter design proceeds in two stages. In the first stage the initial filter pole and zero coefficients are computed. A block diagram is shown in FIG. 2A. The hearing aid processing is turned off, and white noise probe signal 216 is injected into the system instead. During the e.g. 250-msec noise burst, the poles and zeroes of the entire system transfer function are determined using an adaptive equation-error procedure. The system transfer function being modeled consists of the series combination of the amplifier 218, receiver 220, acoustic feedback path 222, and microphone 202. The equation-error procedure uses FIR filter 206 after the microphone to cancel the poles of the system transfer function, and uses FIR filter 212 to duplicate the zeroes of the system transfer function. Delay 214 represents the broadband delay in the system. Filters 206 and 212 are simultaneously adapted during the noise burst using an LMS algorithm 204, 210. The objective of the adaptation is to minimize the error signal produced at the output of summation 208. When the ambient noise level is low and its spectrum relatively white, minimizing the error signal generates an optimum model of the poles and zeroes of the system transfer function. In the preferred embodiment, a 7-pole/7-zero filter is used.

The pole coefficients are then frozen and undergo no further changes. In the second stage of the IIR filter design, the zeroes of the IIR filter are adapted to correspond to the modified poles. A block diagram of this operation is shown in FIG. 2B. The white noise probe signal 216 is injected into the system for a second time, again with the hearing aid processing turned off. The probe is filtered through delay 214 and thence through the frozen pole model filter 206 which represents the denominator of the modeled system transfer function. The pole coefficients in filter 206 have been detuned as described in the paragraph above to lower the Q values of the modeled resonances. The zero coefficients in filter 212 are now adapted to reduce the error between the actual feedback system transfer function and the modeled system incorporating the detuned poles. The objective of the adaptation is to minimize the error signal produced at the output of summation 208. LMS adaptation algorithm 210 is again used. Because the zero coefficients computed during the first noise burst are already close to the desired values, the second adaptation will converge quickly. In many instances, the second adaptation produces minimal changes in the zero filter coefficients. In these cases the second stage can be safely eliminated.

FIG. 3 (Prior Art) is a block diagram showing the hearing aid during operation, including the running adaptation of the zero filter coefficients, in a first embodiment of the present invention. The series combination of the frozen pole filter 206 and the zero filter 212 gives the model transfer function G(z) determined during start-up. The coefficients of the zero model filter 212 are initially set to the values developed during the start-up procedure, but are then allowed to adapt. The coefficients of the pole model filter 206 are kept at the values established during start-up and no further adaptation of these values takes place during normal hearing aid operation. The hearing aid processing is then turned on and the zero model filter 212 is allowed to continuously adapt in response to changes in the feedback path as will occur, for example, when a telephone handset is brought up to the ear.

During the running processing shown in FIG. 3, no separate probe signal is generally used, since it would be audible to the hearing aid wearer. The coefficients of zero filter 212 are updated adaptively while the hearing aid is in use. The output of hearing aid processing 402 is used as the probe. In order to minimize the computational requirements, the LMS adaptation algorithm is preferably used by block 210. More sophisticated adaptation algorithms offering faster convergence are available and could be used instead, but such algorithms generally require much greater amounts of computation and therefore are not yet as practical for a hearing aid. The adaptation is driven by error signal e(n) which is the output of the summation 208. The inputs to the summation 208 are the signal from the microphone 202, and the feedback cancellation signal produced by the cascade of the delay 214 with the all-pole model filter 206 in series with the zero model filter 212. The zero filter coefficients are updated using LMS adaptation in block 210. The LMS weight update on a sample-by-sample basis is given by $$w(n+1)=w(n)+2\mu e(n)g(n)$$

where w(n) is the adaptive zero filter coefficient vector at time n, e(n) is the error signal, and g(n) is the vector of present and past outputs of the pole model filter 206. The weight update for block operation of the LMS algorithm is formed by taking the average of the weight updates for each sample within the block.

Figure 4:
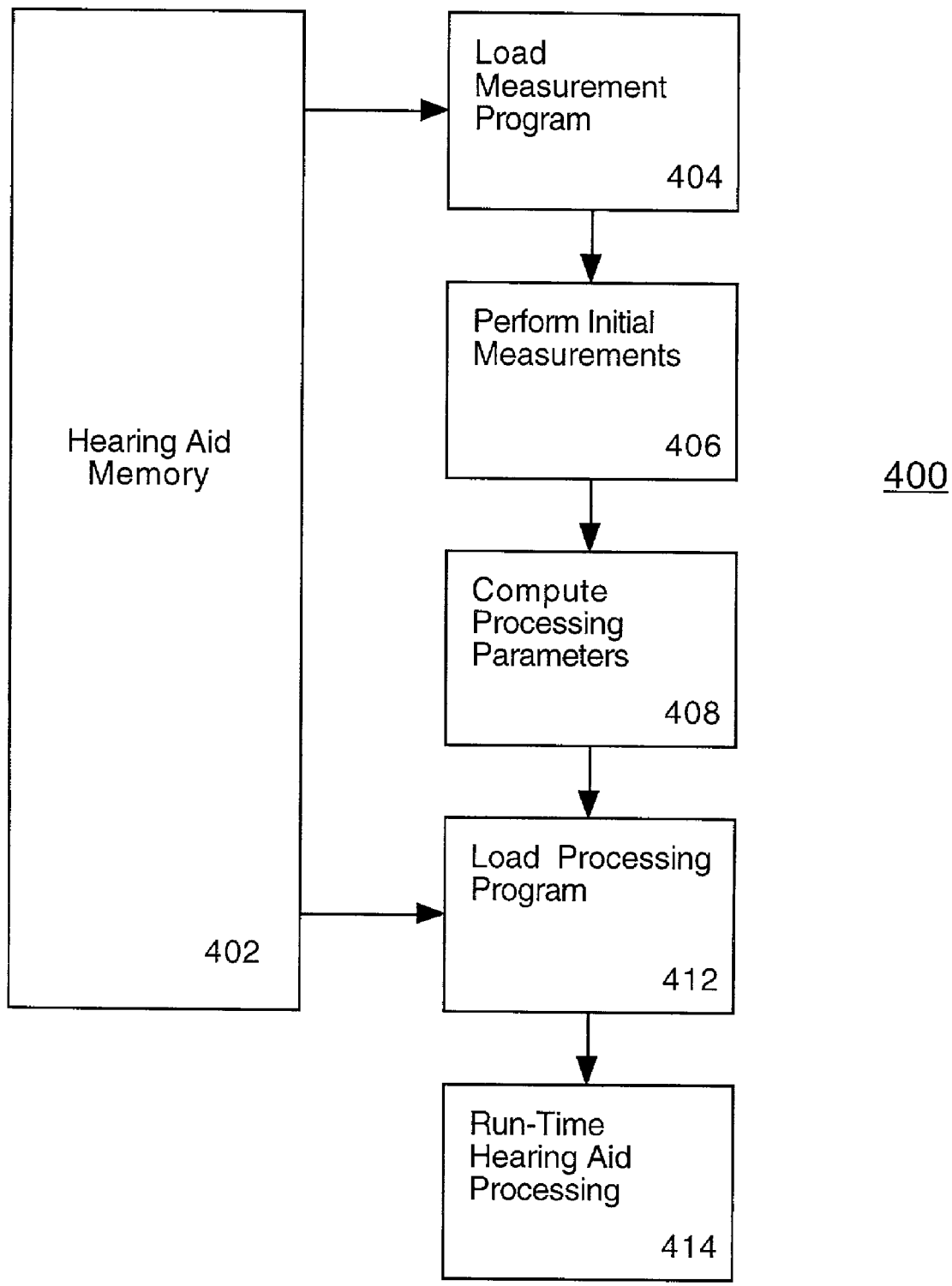
FIG. 4 is a flow diagram showing a first integrated hearing aid performance measurement and initialization method according to the present invention.
Figure 5:
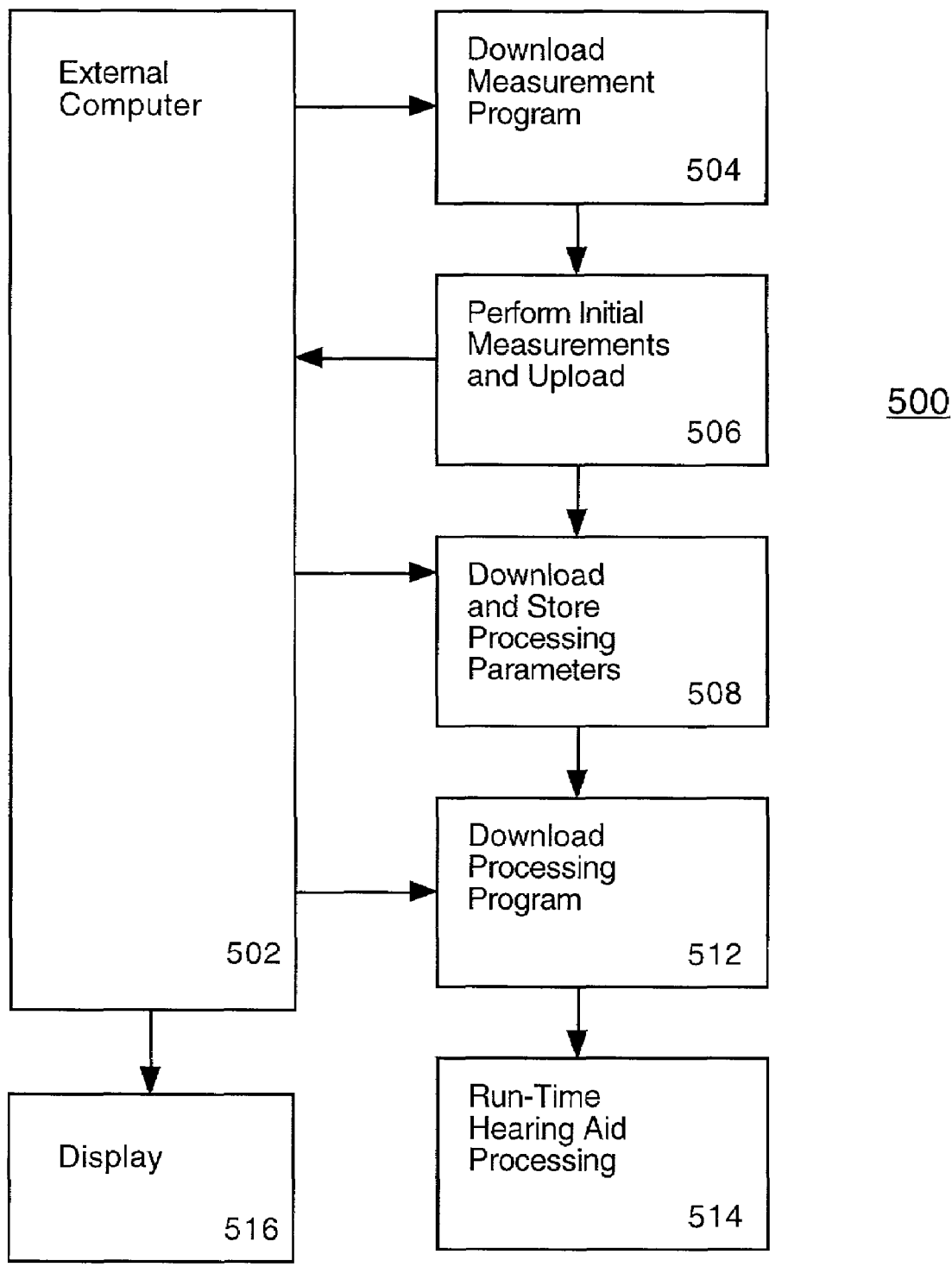
FIG. 5 is a flow diagram showing a second partially integrated hearing aid performance measurement and initialization method according to the present invention.

FIG. 4 is a flow diagram showing a first integrated hearing aid performance measurement and initialization method 400. The hearing aid might be very similar to that shown in FIG. 3, but the hearing aid processor is a programmable DSP. The initial processing steps 404–408 shown in FIG. 4 are preferably run prior to the run time operation 414 of the hearing aid, as an initialization process. This initialization may be performed once, or each time the hearing aid is turned on, or at other times. In FIG. 4, the initialization process is entirely integrated within the hearing aid. FIG. 5 shows an alternative embodiment in which some or all of the processing is offloaded to a host computer. For example, the host computer could estimate the physical feedback path.

In the example of FIG. 4, the code used to perform measurements and set initialization parameters is resident in hearing aid memory 403, and all processing is performed within the hearing aid.

Figure 6:
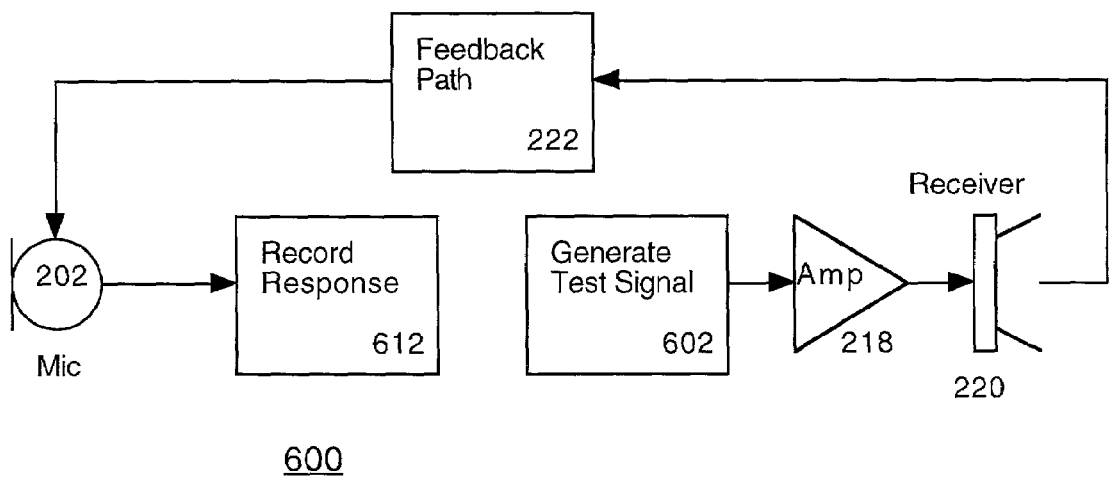
FIG. 6 is a block diagram showing a first configuration for performing the measurement steps of FIGS. 4 and 5.
Figure 7:
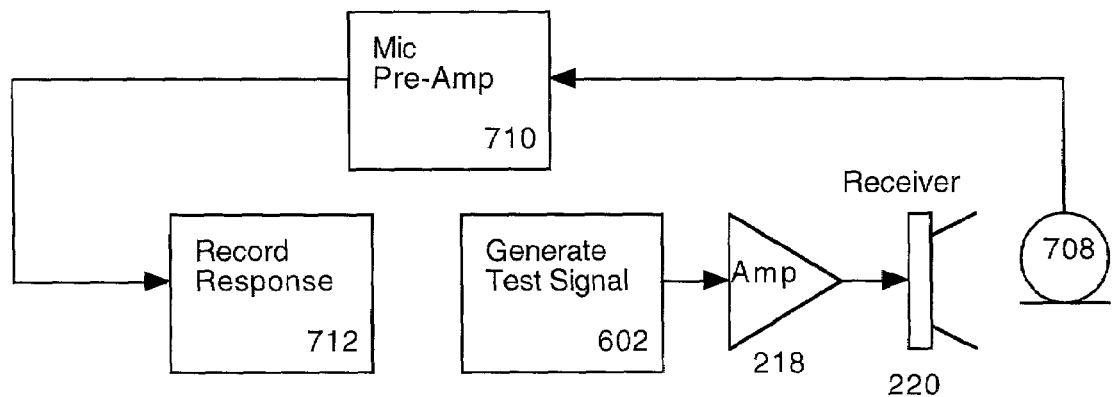
FIG. 7 is a block diagram showing a second configuration for performing the measurement steps of FIGS. 4 and 5.
Figure 8:
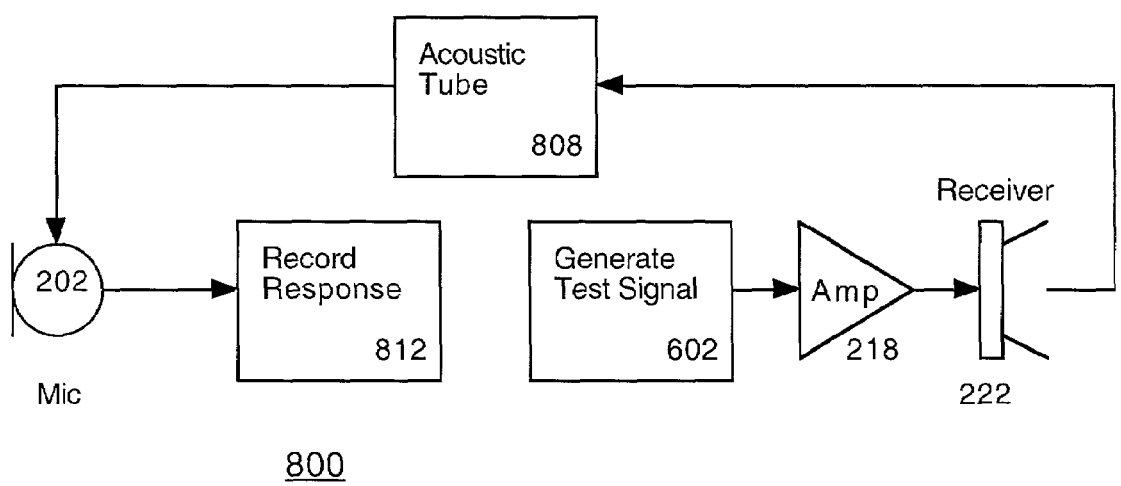
FIG. 8 is a block diagram showing a third configuration for performing the measurement steps of FIGS. 4 and 5.

In step 404, the measurement program is loaded from hearing aid memory 403. Preferably, this program is stored in some form of rewritable memory, so the program can be updated if desired. Step 406 performs measurements of hearing aid performance, for example transfer functions of various combinations of hearing aid elements. FIGS. 6–8 illustrate various measurement configurations which could be employed. In step 408, processing parameters are computed from these measurements. In step 412, the hearing aid run time program is loaded into operating memory, and in step 414, run time hearing aid processing begins.

Note that the two step procedure of loading the initialization code followed by loading the run time code is most appropriate when the hearing aid has a limited amount of program memory; if enough memory is available, the initialization and run time code can be combined into a single program.

FIG. 5 is a flow diagram showing a second, partially integrated, hearing aid performance measurement and initialization method. In this embodiment, the hearing aid establishes a bidirectional link, or communication conduit, with a host computer 502 to download program code and process the measurements. Display 516 displays maximum stable gain curves, hearing aid response curves, and the like. In step 504 the measurement program is downloaded from host computer 502. The hearing aid DSP runs the program and acquires data in step 506, and may also partially process the data. The raw or partially processed data is then sent up to host computer 502, which computes some or all of the processing parameters. Step 508 stores the processing parameters for use by the run time processing program. The run time code is then downloaded to the hearing aid in step 512. Real time processing begins in step 514.

The method shown in FIG. 5 might be used when there is simply not enough storage memory in the hearing aid for both the measurement program and the run time program. Thus, each must be separately loaded into the hearing aid when needed. In general, the initialization is performed only once in the scenario shown in FIG. 5, since an external computer is required to load the two programs. However, the process of FIG. 5 could be repeated, if better initialization or run time programs became available, for example.

FIGS. 6–8 show configurations for performing measurement steps 406 and 506 of FIGS. 4 and 5. FIGS. 11–16 illustrate examples of computing processing parameters, either in the hearing aid or in a host computer.

FIG. 6 is a block diagram showing a first measurement configuration. The characteristics of the feedback path, which includes the amplifier 218, receiver 220, and microphone 202 along with the acoustic and mechanical feedback 222, can be measured by exciting the system with a test signal 602 (e.g. Probe 216) and recording the response 612 at the hearing aid microphone 202.

The impulse response of the feedback path can be obtained, for example, by using a periodic maximal-length sequence as the probe and accumulating the corresponding periods of the microphone response. The circular correlation of the microphone response with one period of the excitation will then give the impulse response of the feedback path. System identification techniques can then be used to produce an all-zero, all-pole, or pole-zero model of the feedback path from the impulse response. An alternative would be to excite the system with a white noise probe sequence and adapt a set of filter coefficients to produce the model of the feedback path.

FIG. 7 is a block diagram showing a second configuration for performing measurement steps 406 and 506 of FIGS. 4 and 5. The characteristics of receiver 220 can be determined using the configuration of FIG. 7. As in the case of the FIG. 6 configuration, a test signal is generated by block 602 which passes through amplifier 218 and receiver 220. However, in this configuration, a calibrated microphone 708 is electrically connected to the hearing aid input via pre-amp 710, thus bypassing the feedback path and the hearing aid microphone. The signal is recorded at 712.

A maximal-length sequence can be used as the excitation, and the impulse response of receiver 220 determined from the output of the calibrated external microphone connected to the audio input of the hearing aid. Or, as in the case of the feedback path estimation shown in FIG. 6, a white noise excitation can be used and a set of filter coefficients adapted to produce a model of the receiver response.

If only the magnitude frequency response is desired, the system can be excited with a sine-wave sweep and the response recorded at the hearing aid input, or individual tones can be used with the magnitude at each frequency determined at the hearing aid input. Distortion can be estimated by increasing the level of the sinusoids and measuring the power at the frequencies of the harmonics, or a noise signal can be used to measure the coherence between the excitation signal and the signal recorded at the hearing aid input.

The minimum digital signal level that drives the amplifier or receiver into saturation can be determined by increasing the level of a sinusoid excitation and observing the maximum output signal level. The maximum receiver output signal level for the D/A converter input at full scale can be determined by generating a sinusoid at full scale and measuring the output signal power.

FIG. 8 is a block diagram showing a third configuration for performing the measurement steps 406 and 506 of FIGS. 4 and 5. The system shown in FIG. 8 can be used to estimate the characteristics of microphone 202 once the receiver impulse response or transfer function has been measured. Receiver 220 is connected directly to microphone 202 via a short acoustic tube 808, so the feedback path is bypassed but amplifier 218, receiver 220, and microphone 202 are included. Since the amplifier-receiver characteristics are already known, only the microphone remains to be measured. A maximal-length sequence, white noise, or a sinusoidal sweep or a set of tones can be used to measure the overall system response, after which the known receiver characteristics are divided out to produce the estimate of the microphone response.

There are several ways in which the measurements can be used to adjust the processing parameters. In a feedback cancellation system such as that shown in FIG. 3, for example, the impulse response of the feedback path can be used as the input to a system identification procedure to produce a nonvarying all-pole, all-zero, or pole-zero filter to model the feedback path or to provide the starting filter coefficients for an adaptive all-zero or pole-zero model. Receiver measurements made in an acoustic coupler can be used on the production line to check that the receiver sensitivity, maximum output signal level, frequency response, and distortion are within specifications. Differences in frequency response could then be used, for example, to adjust equalization used to compensate for irregularities in the receiver frequency response. An external microphone connected to a probe tube inserted in the ear canal along with the hearing aid earmold could be used to provide equalization for the receiver as it will be used in situ. The microphone response measurements can be used to provide equalization for the microphone in a manner similar to that used for the receiver. The receiver and microphone response and calibration curves can also be used to adjust compression parameters for each hearing aid so that the amplified input signal never exceeds the maximum digital level that can be handled by the DAC without distortion.

Figure 9:
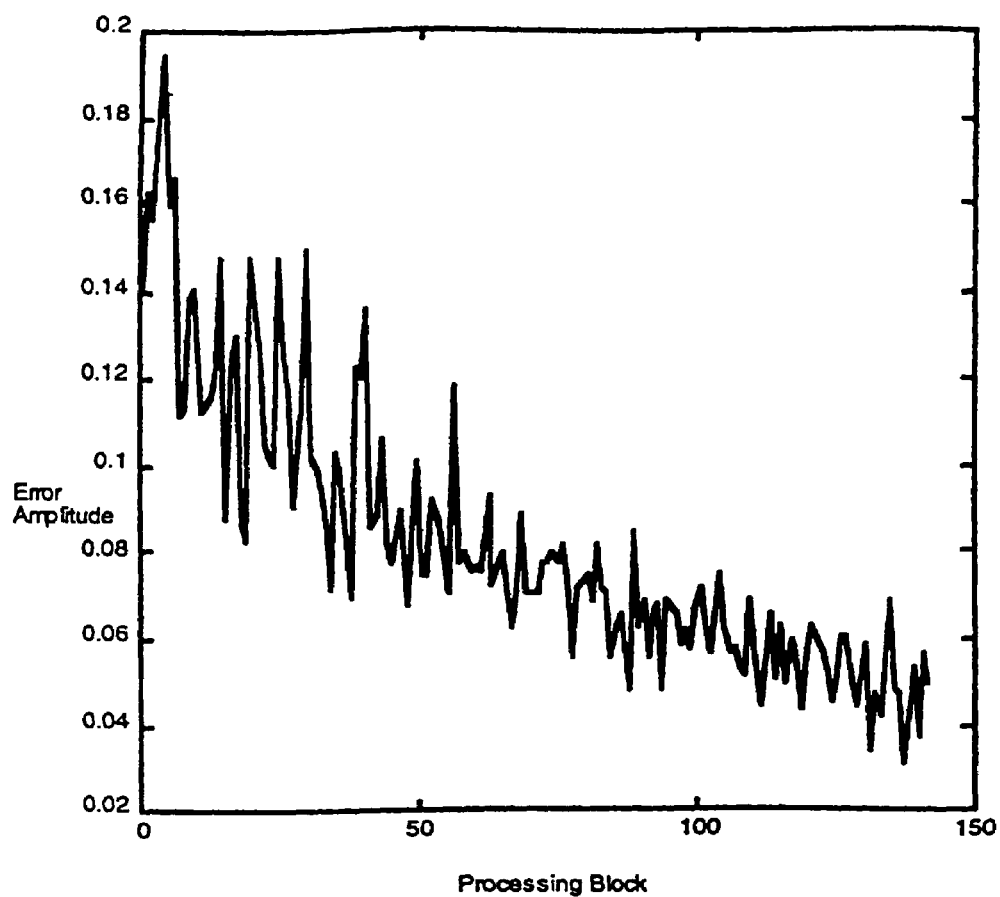
FIG. 9 is a plot of the error signal during initial adaptation of the embodiment of FIG. 2A.

FIG. 9 is a plot of the error signal during initial adaptation, for the embodiment of FIG. 2A. The figure shows the error signal 104 during 500 msec of initial adaptation. The equation-error formulation is being used, so the pole and zero coefficients are being adapted simultaneously in the presence of white noise probe signal 216. The IIR feedback path model for this example consists of 4 poles and 7 zeroes, with a bulk delay adjusted to compensate for the delay in the block processing. These data are from a real-time implementation using a Motorola 56000 family processor embedded in an AudioLogic Audallion and connected to a Danavox behind the ear (BTE) hearing aid. The hearing aid was connected to a vented earmold mounted on a dummy head. Approximately 12 dB of additional gain was obtained using the adaptive feedback cancellation design of FIG. 3.

Figure 10:
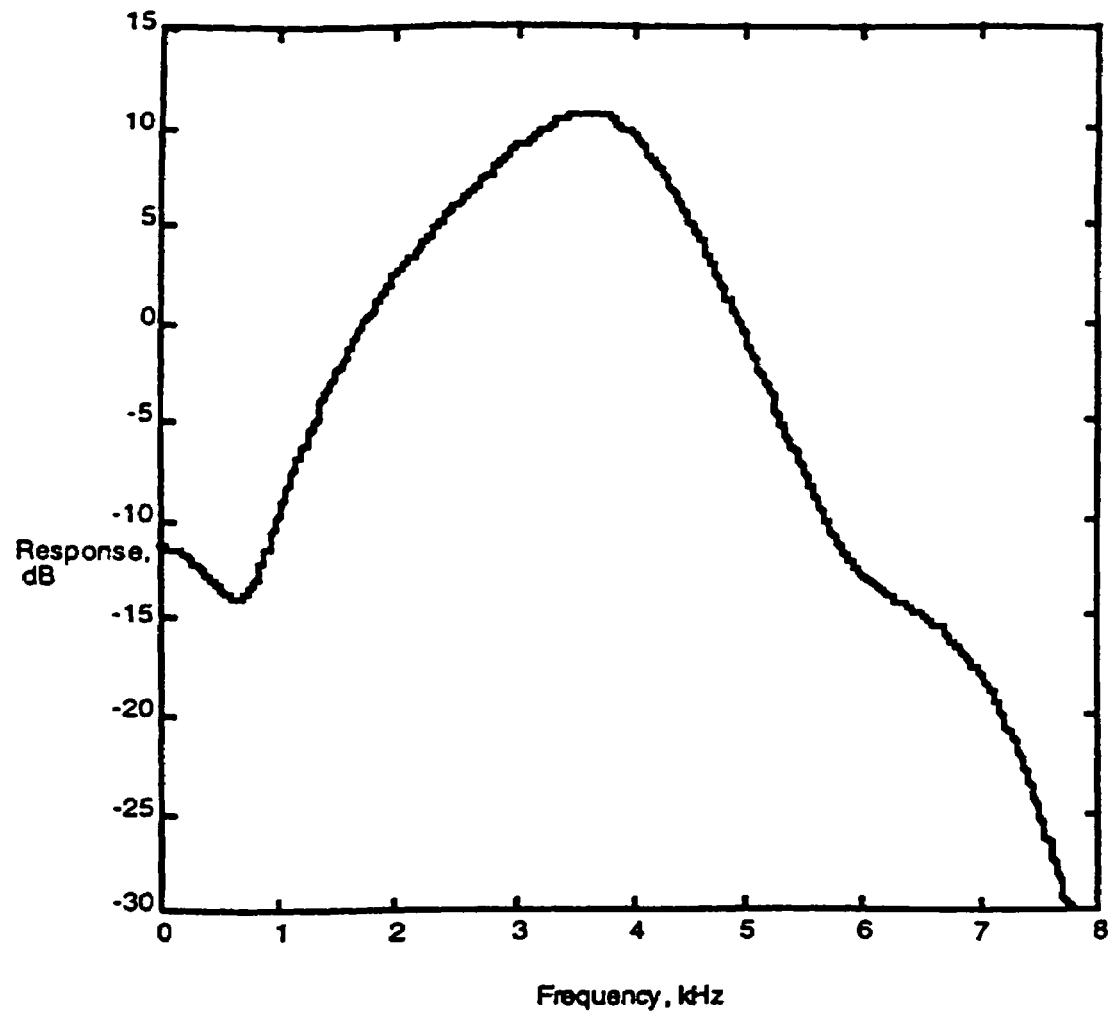
FIG. 10 is a plot of the magnitude frequency response of the IIR filter after initial adaptation, for the embodiment of FIG. 3.

FIG. 10 is a plot of the frequency response of the IIR filter after initial adaptation, for the embodiment of FIG. 3. The main peak at 4 KHz is the resonance of the receiver (output transducer) in the hearing aid. Those skilled in the art will appreciate that the frequency response shown in FIG. 10 is typical of hearing aids having a wide dynamic range and expected shape and resonant value.

Figure 11:
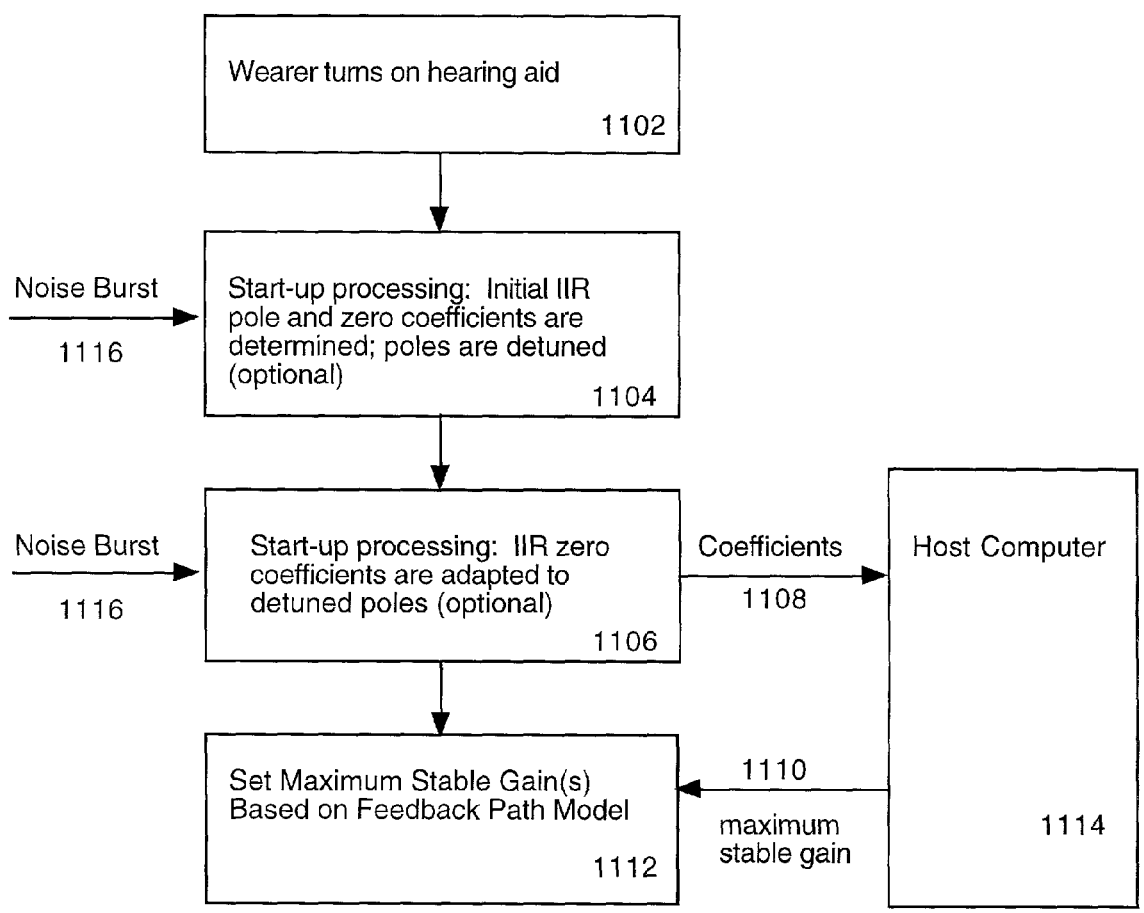
FIG. 11 is a flow diagram showing a process for setting maximum stable gain, for the embodiment of FIG. 3, during initialization and fitting.

FIG. 11 is a flow diagram showing an example of a process for setting maximum stable gain in hearing aids according to the present invention. In general, this maximum gain is set once, at the time the hearing aid is fitted and initialized for the patient, based upon the the feedback path model determined during initialization. The procedure is to perform the initial filter adaptation shown in FIGS. 2A and 2B in steps 1102–1106, transfer the filter coefficients 1108 to a host computer 1114, which performs an analysis that gives the estimated maximum stable gain 1110 as a function of frequency. Step 1112 then sets the maximum stable gain (or gain versus frequency) of the hearing aid. Noise bursts 1116 could be the test signal 602 or probe signal 216.

The initial adaptation of the feedback cancellation filter (performed in steps 1102 through 1106) gives an estimate of the actual feedback path, represented by the filter coefficients derived in steps 1102 through 1106. The maximum stable gain for the feedback cancellation turned off can be estimated by taking the inverse of this estimated feedback path transfer function. With the feedback cancellation turned on, the maximum stable gain is estimated as a constant (greater than one) times the gain allowed with the feedback cancellation turned off. For example, the feedback cancellation might give a maximum gain curve that is approximately 10 dB higher than that possible with the feedback cancellation turned off. The estimated maximum gain as a function of frequency can then be used to set the gains used in the hearing aid processing so that the system remains stable under normal operating conditions.

The maximum stable gain can also be determined for different listening environments, such as using a telephone. In this case, an initialization would be performed for each environment of interest. For example, for telephone use, a handset would be brought up to the aided ear and the maximum stable gain would then be determined as shown in FIG. 10. If the maximum stable gain is less for telephone use than for normal face-to-face conversation, the necessary gain reduction can be programmed into a telephone switch position on the hearing aid or remote control.

More specifically, the maximum gain can be estimated by host computer 1114 as follows. If the feed-forward path through the vent is ignored, the hearing aid output transfer function is given by:

$$Y = \frac{HMAR}{1 + H(W - MARB)} * X$$

where:
 X=input signal
 H=hearing aid gain versus frequency
 M=microphone
 A=amplifier
 R=receiver
 B=feedback path, and
 W=adaptive feedback path model and all variables are functions of frequency.

Assuming there is no feedback cancellation, W=0, and that the hearing aid gain is set to maximum gain Hmax at all frequencies gives:

$$Y = \frac{HmaxMAR}{1 - Hmax(MARB)} * X$$

The system will be stable if |Hmax(MARB)|<1, so that the maximum gain can be expressed as:

$Hmax=1/|MARB|$

Note that when the hearing aid is turned on, the adaptive filter initialization produces $W_0 \cong MARB$ after initial adaptation during the noise burst. Thus we have:

$Hmax \cong 1/|W_0|$

Thus, Hmax for no feedback cancellation can be estimated directly from the initial feedback model. The maximum gain for the system with feedback cancellation is estimated as δ dB above the Hmax determined above, for example δ=10 dB. The value of δ can be estimated from the error signal at the end of the initial adaptation in comparison to the error signal at the start of the initial adaptation.

Figure 12:
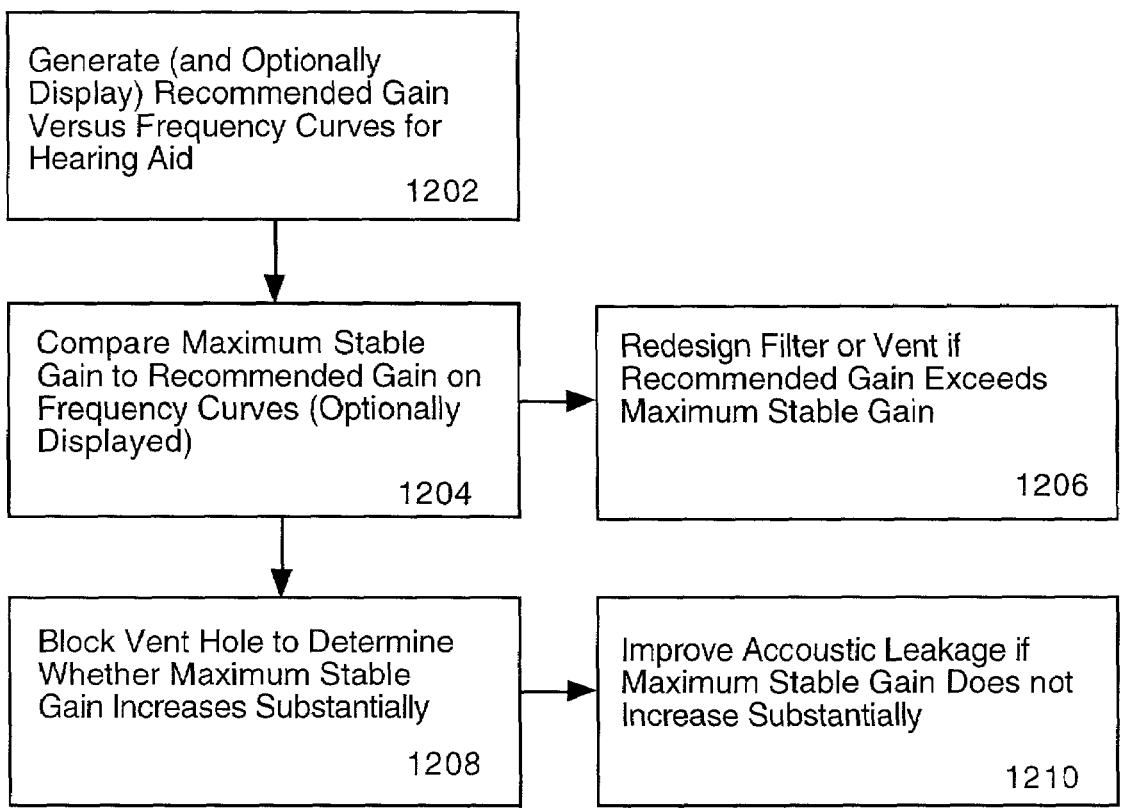
FIG. 12 is a flow diagram showing a process for assessing a hearing aid based on the maximum stable gain, for the embodiment of FIG. 3, during initialization and fitting.

FIG. 12 is a flow diagram showing a process for assessing a hearing aid according to the present invention during initialization and fitting, based on the maximum stable gain determined, for example, as shown in FIG. 11. For example, the maximum stable gain can be used to assess the validity of the earmold and vent selection in a BTE hearing aid or in the shell of an ITE or CIC hearing aid. The analysis of the client's hearing loss (based, for example, on an audiogram) produces a set of recommended gain versus frequency curves for the hearing aid, step 1202. These curves, and maximum stable gain curves, may optionally be displayed on display 516 (see FIG. 5). Step 1204 compares the recommended gain versus frequency curves to the maximum stable gain curve. If the recommended gain exceeds the maximum stable gain, the hearing aid fitting may drive the system into instability and "whistling" may result.

Step 1206 indicates that the hearing aid fitting may need to be redesigned. The maximum stable gain is affected by the feedback path, so reducing the amplitude of the feedback signal will increase the maximum stable gain; in a vented hearing aid, the difference between the recommended and maximum stable gain values can be used to determine how much smaller the vent radius should be made to ensure stable operation.

The initialization and maximum stable gain calculation can also be used to test the hearing aid fitting for acoustic leakage around the BTE earmold or ITE or CIC shell. The maximum stable gain is first determined as shown in FIG. 11 for the vented hearing aid as it would normally be used. The vent opening is then blocked with putty, and the maximum stable gain again determined in step 1208. The maximum stable gain for the blocked vent should be substantially higher than for the open vent; if it is not, then acoustic leakage is making an important contribution to the total feedback path and the fit of the earmold or shell in the ear canal needs to be checked, as indicated in step 1210.

Figure 13:
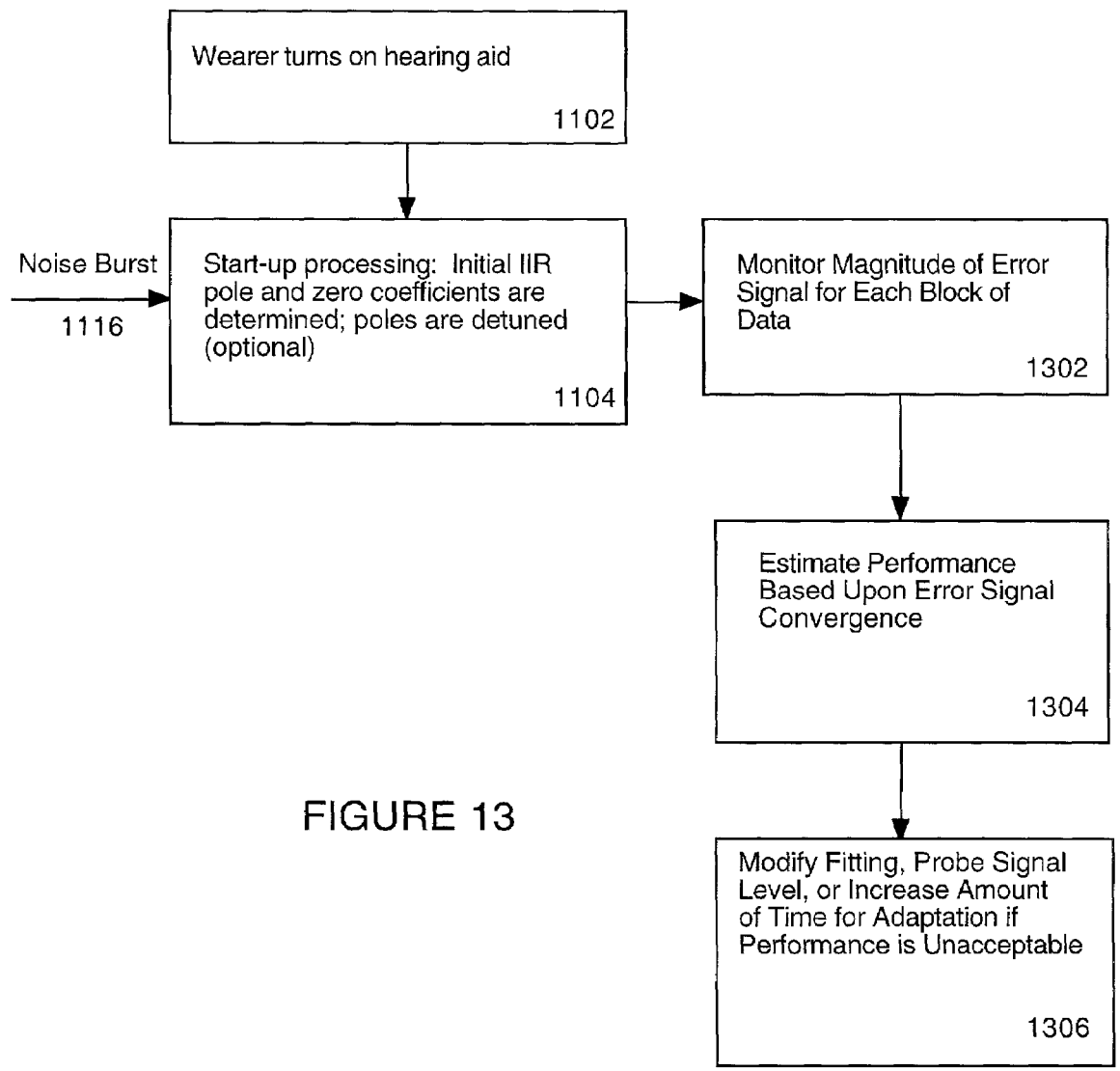
FIG. 13 is a flow diagram showing a process for using the error signal in the adaptive system as a convergence check, for the embodiment of FIG. 3, during initialization and fitting.

FIG. 13 is a flow diagram showing a process for using the error signal in the adaptive system as a convergence check during initialization and fitting. The error signal in the adaptive system is the signal output by the microphone minus the signal from the feedback path model filter cascade. This signal decreases as the adaptive filters converge to the model of the feedback path. For example, a feedback cancellation system may be intended to provide 10–12 dB of feedback cancellation. The magnitude of the error signal can be computed for each block of data during the adaptation, and the signal stored during adaptation read back to the host computer when the adaptation is assumed to be complete. If the plot of the error signal versus time does not show the desired degree of feedback cancellation, the hearing aid dispenser has the option of repeating the adaptation, increasing the probe signal level, or increasing the amount of time used for the adaptation. The fitting software can be designed to fit a smooth curve to the error function, and to then extrapolate this curve to determine the intensity or time values, or combination of values, needed to give the desired feedback cancellation performance. The amount of feedback cancellation can be estimated from the ratio of the error signal at the start of the adaptation to the error signal at the end of the adaptation. This quantity can be computed from the plot of the error signal versus time, or from samples of the error signal taken at the start and end of the adaptation.

The process of utilising the error signal in the adaptive system as a convergence check is as follows. The wearer turns on the hearing aid in step 1102. Step 1104 comprises the start up processing step in which initial coefficients are determined (detuning the poles is optional).

Steps 1302 through 1304 would generally be performed by host computer 1114 for example, though they could be incorporated into the hearing aid as an alternative. Step 1302 monitors the magnitude of the error signal (the output from adder 208 in FIG. 3 for example) for each block of data. Step 1304 compares the curve of error signal versus time obtained in step 1302 with model curves which indicate the desired performance of the hearing aid. Step 1306 indicates that the hearing aid fitting may need to be redesigned if the error versus time curves strays too far from the model curves, or if the amount of feedback cancellation is insufficient.

Figure 14:
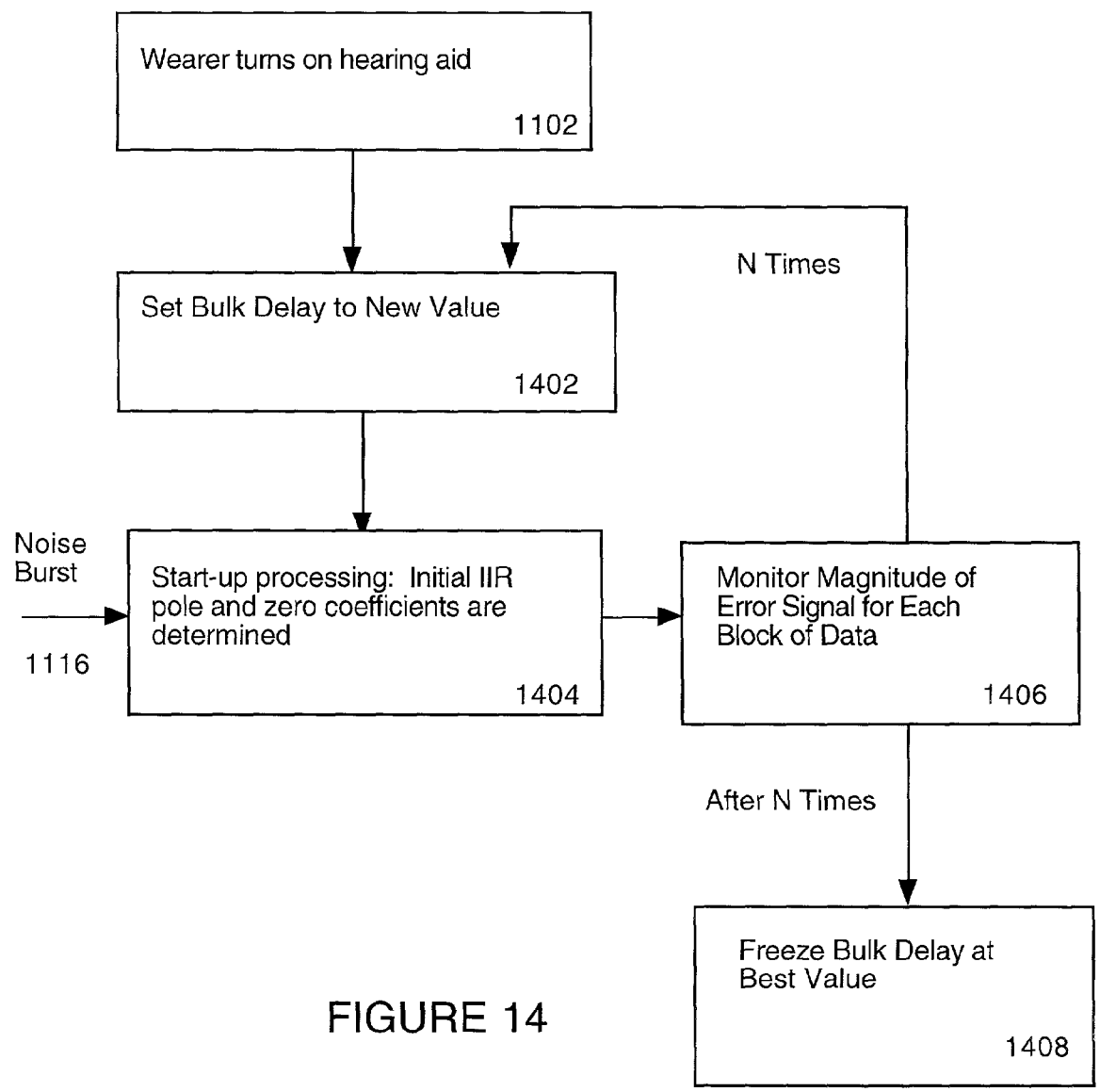
FIG. 14 is a flow diagram showing a process for using the error signal to adjust the bulk delay in the feedback model, for the embodiment of FIG. 3, during initialization and fitting.

FIG. 14 is a flow diagram showing a process for using the error signal to adjust the bulk delay (block 214 in FIG. 3) in the feedback model during initialization and fitting. The initial adaptation is performed for two or more different values of the bulk delay in the feedback path model, with the error signal for each delay value computed and transferred to host computer 1114. The delay giving the minimum error is then set in the feedback cancellation algorithm. A search routine can be used to select the next delay value to try given the previous delay results; an efficient iterative procedure then quickly finds the optimum delay value.

In the embodiment of FIG. 14, the wearer turns on the hearing aid in step 1102. The bulk delay is set to a first value in step 1402, and start up processing is performed in step 1404 to determine initial coefficients. Step 1406 monitors the magnitude of the error signal over time for the first value of the bulk delay. This process is repeated N times, setting the bulk delay to a different value each time. When all desired values have been tested, step 1408 sets the value of the bulk delay to the optimal value. Steps 1406 and 1408 would generally be performed by host computer 1114.

Figure 15:
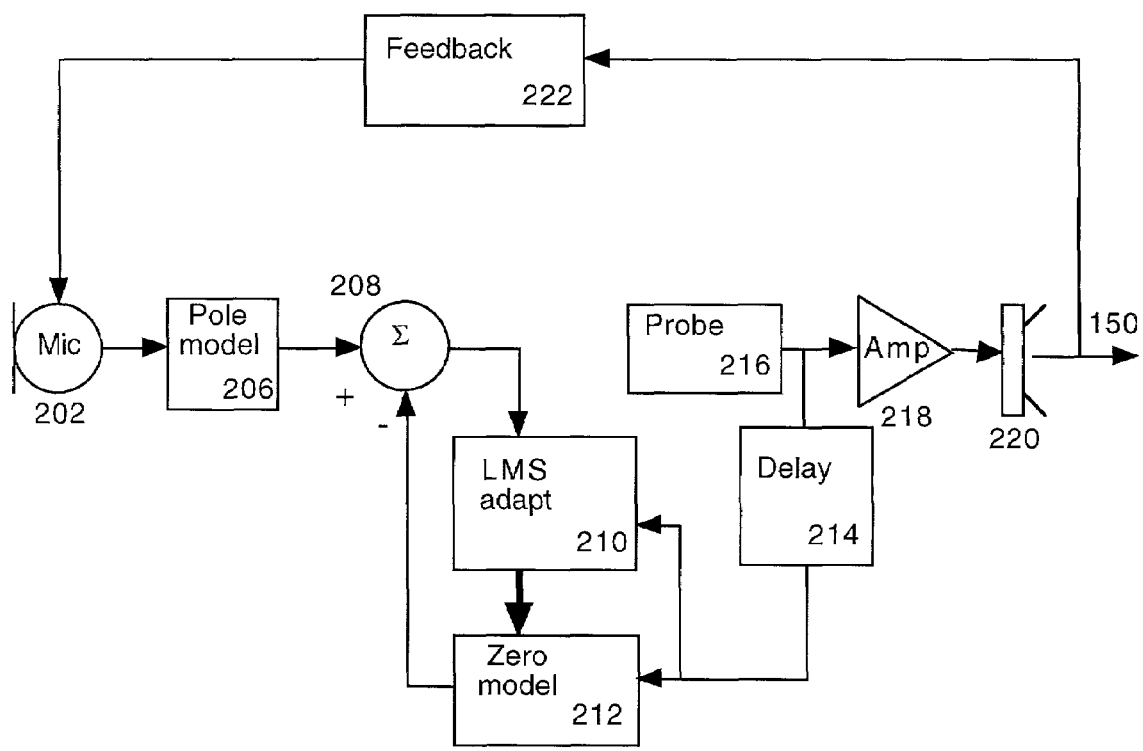
FIG. 15 is a block diagram showing a process for estimating bulk delay by monitoring zero coefficient adaptation, for the embodiment of FIG. 3, during initialization and fitting.

FIG. 15 is a block diagram showing a different process for estimating bulk delay, by monitoring zero coefficient adaptation during initialization and fitting. During start up processing the system adapts the pole and zero coefficients to minimize the error in modeling the feedback path. The LMS equation (computer in block 210) used for the zero coefficient adaptation is essentially a cross-correlation, and is therefore an optimal delay estimator as well. The system for estimating the delay shown in FIG. 15 preferably freezes pole filter 206, in order to free up computational cycles for adapting an increased number of zero filter 212 coefficients (to better ensure that the desired correlation peak is found). The preliminary bulk delay value in 214 is set to a value which will give a peak within the zero filter window. Then the zero filter coefficients are adapted, and a delay depending on the lag corresponding to the peak value coefficient is added to the preliminary bulk delay, resulting in the value assigned to bulk delay 214 for subsequent start up and running processing.

In a preferred embodiment, the normal 8 tap zero filter length is increased to 16 taps for this process, and the the zero filter is adapted over a 2 second noise burst.

Figure 16:
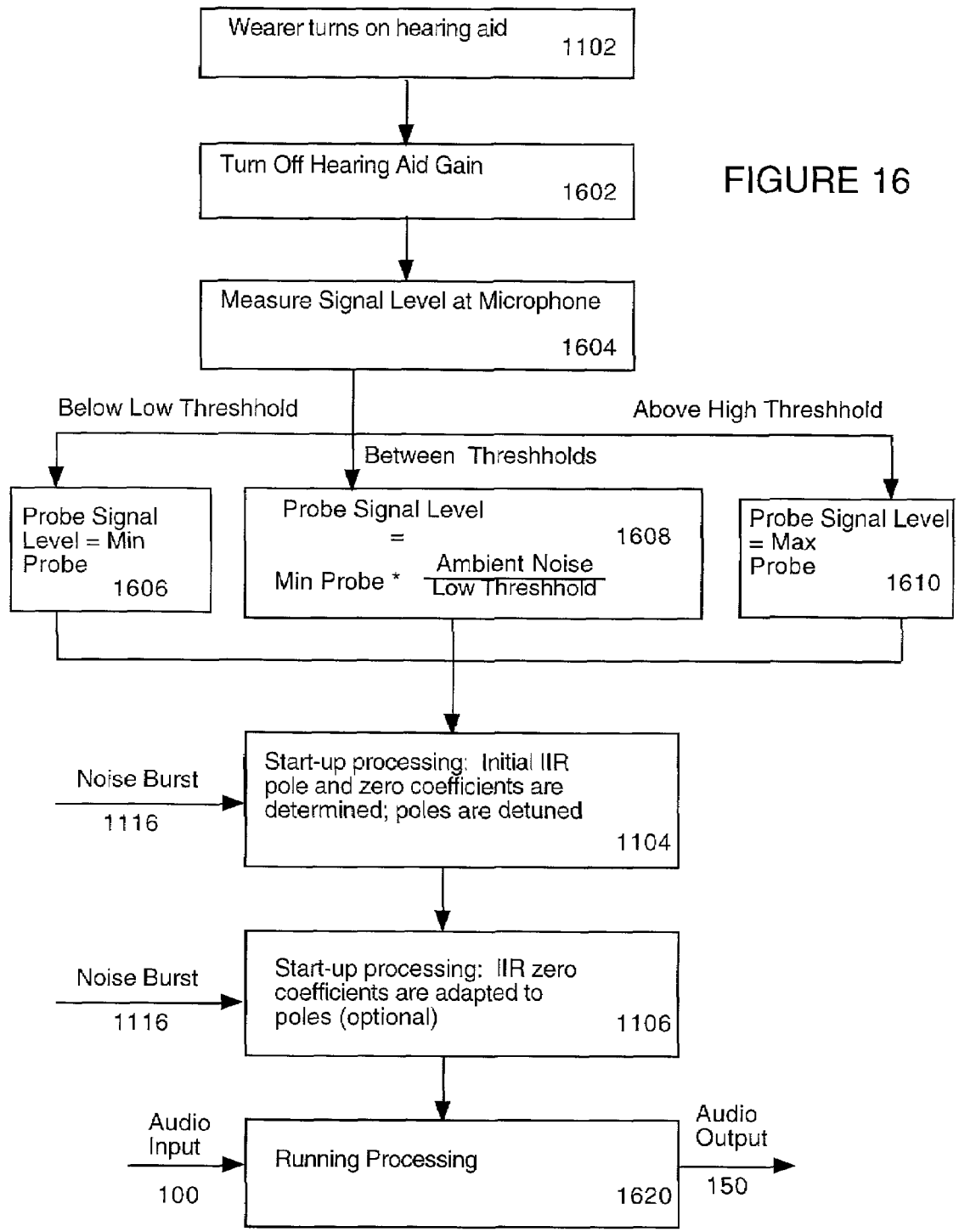
FIG. 16 is a flow diagram showing a process for adjusting the noise probe signal based upon ambient noise, for the embodiment of FIG. 3, either during initialization and fitting or during start up processing.

FIG. 16 is a flow diagram showing a process for adjusting the noise probe signal based upon ambient noise, either during initialization and fitting or during start up processing. The objective is to minimize the annoyance to the hearing aid user by using the least intense probe signal that will provide the necessary accuracy in estimating the feedback path model. The procedure is to turn on the hearing aid (in step 1102), turn the hearing aid gain off (in step 1602), and measure the signal level at the hearing aid microphone (step 1604). If the ambient noise level is below a low threshold, a minimum probe signal intensity is used (step 1606). If the ambient noise level is above the low threshold and below a high threshold, the probe signal level is increased so that the ratio of the probe signal level to the minimum probe level is equal to the ratio of the ambient noise level to its threshold (step 1608). The probe signal level is not allowed to exceed a maximum value chosen for listener comfort. If the ambient noise level is above the high threshold, step 1610 limits the probe signal level to a predetermined maximum level. The initial adaptation then proceeds in steps 1104 and 1106 using the selected probe signal intensity. This procedure ensures proper convergence of the adaptive filter during the initial adaptation while keeping the loudness of the probe signal to a minimum.

While the exemplary preferred embodiments of the present invention are described herein with particularity, those skilled in the art will appreciate various changes, additions, and applications other than those specifically mentioned, which are within the spirit of this invention. In particular, the present invention has been described with reference to a hearing aid, but the invention would equally applicable to public address systems, speaker phones, or any other electro-acoustical acoustical amplification system where feedback is a problem.

What is claimed is:

1. A method of fitting a hearing aid to a hearing aid user comprising the steps of:
 a) engaging the hearing aid with the user's ear;
 b) establishing a bidirectional data communication link between a host processor and the hearing aid;
 c) causing the hearing aid to generate an acoustic test signal within the hearing aid;
 d) recording an input signal at the hearing aid input microphone resulting from the fed-back test signal;
 e) transmitting data based upon the recorded signal to the host processor;
 f) computing an estimate of the physical feedback transfer function of the hearing aid from data based upon the recorded signal;
 g) determining a maximum stable gain curve based upon the computed physical feedback transfer function; and
 h) displaying the maximum stable gain curve of the hearing aid on a display screen associated with the host processor.

2. The method of claim 1, further including the steps of:
 providing audiogram data characterizing the hearing loss of the user in the host processor;
 determining prescribed gain characteristics of the hearing aid based upon the audiogram data;
 displaying, on the display screen, at least one hearing aid gain response curve representing the prescribed gain characteristics.

3. The method of claim 1, wherein the hearing aid includes a feedback cancellation system, and further comprising the steps of:
 displaying a first maximum stable gain curve representing a maximum achievable gain with the feedback cancellation means disabled;
 displaying a second maximum stable gain curve representing a maximum achievable gain with the feedback cancellation means enabled.

4. The method of claim 3, further comprising the steps of:
 determining initial filter coefficients of the adaptive filter within the feedback cancellation system based upon the estimate of the physical feedback transfer function;
 transmitting the initial filter coefficients to the hearing aid; and
 storing the initial filter coefficients in the hearing aid.

5. The method of claim 1 wherein the estimate of the physical feedback transfer function is computed by the host computer.

6. The method of claim 1, further comprising the step of setting a maximum gain in the hearing aid based on the estimate of the physical feedback transfer function.

7. Apparatus for fitting a hearing aid to a hearing aid user comprising:
 a hearing aid having a microphone, a signal processor, and a receiver, and further including a signal generator as part of the hearing aid for generating an audio test signal within the hearing aid, and a recorder for recording the fed back test signal at the microphone;
 a host computer;
 a communication conduit for transmitting data between the hearing aid and the host computer; and
 a display associated with the host computer;
 wherein the hearing aid transmits a signal based upon the recorded fed back test signal to the host computer via the communication conduit;
 wherein the host computer generates a maximum stable gain curve based upon the transmitted signal; and
 wherein the display displays the maximum stable gain curve.

8. The apparatus of claim 7 wherein the host computer further includes means for estimating the physical feedback path transfer function of the hearing aid, and generates the maximum stable gain curve based upon the estimated physical feedback path transfer function.

9. The apparatus of claim 8 wherein the hearing aid further includes feedback cancellation means including an adaptive filter, wherein the host computer generates maximum stable gain curves with the feedback cancellation means enabled and disabled, and wherein the display displays both curves.

10. The apparatus of claim 9, wherein the host computer further computes initial adaptive filter coefficients based upon the estimated physical feedback path transfer function, wherein the host computer transmits the initial coefficients to the hearing aid via the communication conduit, and wherein the hearing aid stores the initial coefficients.

11. The apparatus of claim 8, wherein the host computer generates a maximum hearing aid gain based upon the estimated physical feedback path transfer function, wherein the host computer transmits the maximum gain to the hearing aid via the communication conduit, and wherein the hearing aid stores the maximum gain.

* * * * *

UNITED STATES PATENT AND TRADEMARK OFFICE
CERTIFICATE OF CORRECTION

| | |
|---|---|
| PATENT NO. | : 7,058,182 B2 |
| APPLICATION NO. | : 10/150242 |
| DATED | : June 6, 2006 |
| INVENTOR(S) | : James Mitchell Kates |

It is certified that error appears in the above-identified patent and that said Letters Patent is hereby corrected as shown below:

Column 1, line 32, delete "Englebretson" and insert --Engebretson--.

Column 4, line 6, delete "No. 6,219,4278" and inset --No. 6,219,427--.

Column 5, line 50, delete "403" and insert --402--.

Column 7, line 20, delete "220" and insert --222--.

Column 7, line 22, delete "220" and insert --222--.

Column 10, line 35, delete "strays" and insert --stray--.

Column 11, line 12, delete "the the" and insert --the--.

Column 11, line 44, between "would" and "equally" insert --be --.

Signed and Sealed this

Twenty-ninth Day of May, 2007

JON W. DUDAS
*Director of the United States Patent and Trademark Office*